United States Patent [19]

Athey et al.

[11] Patent Number: 5,587,451
[45] Date of Patent: Dec. 24, 1996

[54] PROCESS FOR PREPARING POLYAZAMACROCYCLES

[75] Inventors: Phillip S. Athey; Garry E. Kiefer, both of Lake Jackson, Tex.

[73] Assignee: The Dow Chemical Company, Midland, Mich.

[21] Appl. No.: 320,620

[22] Filed: Oct. 7, 1994

Related U.S. Application Data

[63] Continuation-in-part of Ser. No. 158,654, Nov. 26, 1993, abandoned.

[51] Int. Cl.$^6$ .................................................. C08G 69/26
[52] U.S. Cl. ...................... 528/345; 528/346; 528/367; 528/368; 540/472; 540/474; 514/79; 514/80; 514/286; 424/901
[58] Field of Search ........................ 528/345, 346, 528/367, 368; 540/472, 474; 514/79, 80, 286; 424/9

[56] References Cited

U.S. PATENT DOCUMENTS

| | | | |
|---|---|---|---|
| 4,639,365 | 1/1987 | Sherry | 424/9 |
| 4,976,950 | 12/1990 | Simon et al. | 424/1.1 |

OTHER PUBLICATIONS

Journal of the American Chemical Society, 96:7, Apr. 3, 1974, pp. 2268–2270.
Organic Synthesis, VI (Collective Volume), 58, 86–97 (1978).
Coor. Chemical Review, 110, 17 (1991), A. Bianchi et al.
Journal of the American Chemical Society, 110, 6266–6267 (1988).
Chemical Abstract, vol. 58:2456a (Belgian Patent 613,063, Feb. 15, 1962).
Chemical Abstract, vol. 100(13): 102774f (Romanian Patent, RO 79987 B, Sep. 30, 1982).
J. Am. Chem. Soc., 96, 2268–2270, 1974.
Chemical Abstracts, 119(18): 194377X.
Z. Anorg. Allg. Chem, 619(7), pp. 1183–1195 (1993).

*Primary Examiner*—James J. Seidleck
*Assistant Examiner*—Duc Truong
*Attorney, Agent, or Firm*—Karen L. Kimble

[57] ABSTRACT

A process for preparing polyazamacrocyclic compounds using a nucleophilic imidazoline with (A) an ethylene oxide or an ethylene carbonate, in an aprotic solvent, followed by intramolecular amination, and then either basic or acidic hydrolysis; or (B) an electrophilic substrate, in a polar solvent, optionally in the presence of a non-nucleophilic base, to form an intermediate, followed by basic hydrolysis; or (C) a electrophilic substrate, in a polar solvent, optionally in the presence of a non-nucleophilic base, followed by prolonged heating in a polar solvent or by treatment with a peroxide solution, followed by basic hydrolysis to form a urea, then basic hydrolysis under pressure; and separating the desired polyazamacrocycle. The compounds so prepared are useful in pharmaceutical applications.

30 Claims, No Drawings

PROCESS FOR PREPARING POLYAZAMACROCYCLES

CROSS REFERENCES TO RELATED APPLICATIONS

This application is a continuation-in-part of our application Ser. No. 158,654, filed Nov. 26, 1993, now abandoned.

BACKGROUND OF THE INVENTION

The role of polyazamacrocycles in various biomedical applications has increased dramatically over the past few years and the tetraazamacrocyclic structure is becoming an important building block for new pharmaceutical agents. Additionally, polyazamacrocycles are excellent chelants which if available at a low cost could be used in various applications for forming chelates, such as for water treatment systems. As a consequence, the tetraazamacrocyclic structure is becoming a fundamental building block in these compounds. In particular, 1,4,7,10-tetraazacyclododecane ("Cyclen")

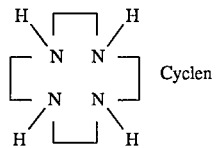

has proven to be one of the most versatile intermediates used in lanthanide-specific chelating agents which are assuming prominance in compounds used in diagnostic and therapeutic medicine. For example, during recent years the increasing importance of paramagnetic lanthanide chelates as contrast enhancement agents (or contrast agents) for magnetic resonance imaging ("MRI") has resulted in the commercial introduction of two Cyclen based products (Dotarem™ by Guerbet and Prohance™ by Squibb). Futhermore, numerous companies are engaged in clinical trials involving potential contrast enhancement agents for MRI which are also based on the Cyclen structure. The market for MRI contrast agents is projected to be about US$700 million by 1998 (Frost & Sullivan, 1994) and Cyclen based products are expected to occupy an important position in this market.

At the present time Parrish Chemical Co. is the only advertised bulk supplier of Cyclen (as the tetraazahydrochloride salt), currently quoting a price of US$6,800/pound. This price reflects the difficulty associated with the currently practiced synthetic method to make Cyclen.

Current methodologies for the synthesis of Cyclen include:

J. E. Richman, T. J. Atkins, *J. Am. Chem. Soc.* 96, 2268–2270 (1974); and

T. J. Atkins, J. E. Richman, W. F. Oettle, *Org. Synth.* VI(collective volume), 58, 86–97 (1978).

The currently practiced methodology for the synthesis of Cyclen [J. E. Richman, T. J. Atkins, *J. Am. Chem. Soc.* 96, 2268–2270 (1974)] involves a multistep protection-deprotection strategy as shown in the following Scheme A.

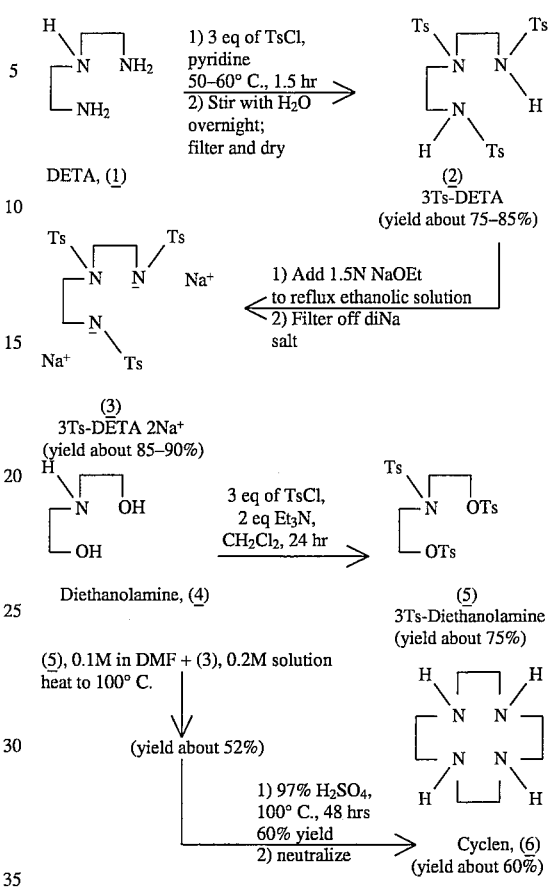

The conventional synthesis of tetraazamacrocyclic ligands involves the reaction of two segments of the target macrocycle in a polar, aprotic solvent, with the most used methodology being the Richman and Atkins' synthesis [J. E. Richman, T. J. Atkins, *J. Am. Chem. Soc.* 96, 2268–2270 (1974)]. In this procedure, one precursor is a preformed salt of a tritosylamide and the other precursor contains sulfonate esters as the leaving groups. (See Scheme A above.) This method has been the one most cited in the literature to prepare saturated polyazamacrocyles containing 3–12 nitrogen atoms.

Final isolation of the macrocycle requires harsh conditions to remove the protecting groups (e.g. tosyl or methanesulfonyl groups). These conditions involve either the use of 97% sulfuric acid or 33% HBr, acetic acid and phenol.

This methodology is adequate, provided that great care is dedicated to the use of very pure, dry starting material. The overall process is tedious, time consuming, low yielding (~20–30% based on the starting amine) and an abundace of tosylate or mesylate salts are generated as waste. Clearly, this described process is time consuming and costly to make commercial quantities of the desired compound.

Another approach which has been tried towards the synthesis of large polyazamacrocycles (meaning those having at least a 14 membered ring) has been the use of metal ion promoted (template) reactions, developed in the early 1960's. Many polyazamacrocycles in their complexed form have been obtained by condensing glyoxal and a polyamine in the presence of a metal ion, mainly Ni(II) and Cu(II). The metal ion can aid in one of two ways: (1) complex and sequester the polyazamacrocyclic product from the reaction equilibrium mixture (in this way the formation of a macrocycle is promoted as its metal complex); or (2) the metal ion influences the steric course of the condensation such that formation of the cyclic product is facilitated [A. Bianchi, M. Micheloni, P. Paoletti, *Coor. Chem. Rev.* 110, 17 (1991)]. Regardless of how the metal ion functions, the application of such chemistry to the synthesis of thirteen-membered (or less) polyazamacrocycles has not been successful, probably due to the incompatibility of the metal size and the eventual cavity size of the desired macrocycle.

Previous synthesis of derivatives of 1,1'-(1,2-ethanediyl)-bis[4,5-dihydro-1H]-imidazole include:

*Chem. Abst.* 100(13):102774f (Romanian Patent, RO 79987 B, 30 Sep. 1982) which discloses alkyl derivatives;

*Chem. Abst.* 58:2456a Belgian Patent 613,063, 15 Feb. 1962 to Armour & Co. which discloses other alkyl derivatives; and WO 92/22535, published 12 Dec. 1992, which discloses additional alkyl derivatives.

A citation which incorrectly indicates that 1,1'-(1,2-ethanediyl)-bis[4,5-dihydro-1H]-imidazole was prepared is:

*Chem. Abst.* 119(18):194377x; however, in the citation, *Z. Anorg. Allg. Chem.* 619(7), 1183–95 (1993), from which the abstract was done, actually the closest compound described and made was 1,2-bis(2-imidazoline-2-yl)ethane.

Clearly, it would be advantageous to have a cheaper, less time consuming process to make the desired polyazamacrocycles. Some of the ways by which these results could be attained are by using less costly starting materials not requiring the Richman-Atkins protection-deprotection method [*J. Am. Chem. Soc.* 96, 2268–2270 (1974) and *Org. Synth.* VI(collective volume), 58, 86–97 (1978)], and by increasing the overall yield of the process.

SUMMARY OF THE INVENTION

The present invention concerns a novel process for preparing polyazamacrocycles from imidazolines. The present process employs novel imidazoline intermediate compounds such as 1,1'-(1,2-ethanediyl)-bis-[4,5-dihydro-1H]-imidazole. The process of this invention utilizes imidazolines in a manner which allows for the use of inexpensive or readily available starting materials, does not require the Richman-Atkins protection-deprotection method [*J. Am. Chem. Soc.* 96, 2268–2270 (1974) and *Org. Synth.* VI(collective volume), 58, 86–97 (1978)], and increases the overall yield of the polyazamacrocycle product. Specifically, the present invention concerns a process for preparing polyazamacrocycles compounds of the formula

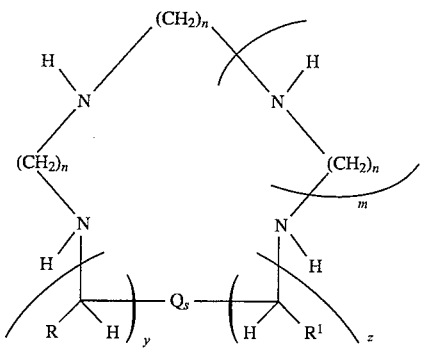

wherein:
each n is independently 2 or 3;
m is 0 or an integer from 1 to 3;

s is 0 or 1;
y is 0 or 1;
z is 0 or 1;
with the proviso that at least 2 of s, y, and z must be 1;

Q is —CH$_2$—, —C(O)— or —CHR;

R is hydrogen, C$_1$–C$_6$ alkyl, —CO$_2$H, —CO$_2$(C$_1$–C$_6$ alkyl) or phenyl;

R$^1$ is hydrogen, —CO$_2$H, —CO$_2$(C$_1$–C$_6$ alkyl), C$_1$–C$_6$ alkyl, C$_1$–C$_6$ alkyl substituted by NH$_2$, NO$_2$, isothiocyanato, semicarbazido, thiosemicarbazido, maleimido, bromoacetamido or OR$^2$, phenyl or phenyl substituted by NH$_2$, NO$_2$, isothiocyanato, semicarbazido, thiosemicarbazido, maleimido, bromoacetamido or OR$^2$; or R and R$^1$ can be taken together to form a phenyl or phenyl substituted by NH$_2$, NO$_2$, isothiocyanato, semicarbazido, thiosemicarbazido, maleimido, bromoacetamido or OR$^2$; and R$^2$ is hydrogen or C$_1$–C$_4$ alkyl;

which comprises reacting an alkylenepolyamine with a formyl equivalent, such as DMF dimethylacetal, either neat or in a nonaqueous solvent to form the unsubstituted imidazoline (9) of the formula:

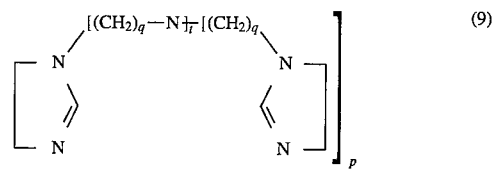

wherein
q is independently 2 or 3;
p is 0 or 1;
t is 0, 1 or 2; and
followed by reacting (9) with:

(A) 1 equivalent of an ethylene oxide or an ethylene carbonate, in an aprotic solvent, to form an alcohol (16) of the formula

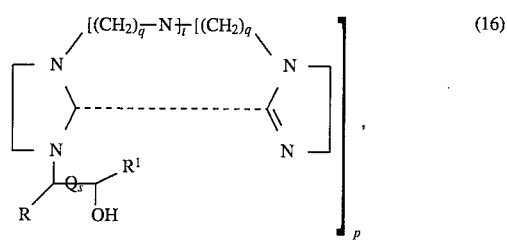

wherein Q, s, R and R$^1$ are defined as for Formula (I) and the dotted line represents the optional presence of a bond; when the bond is present, then t is 0, q is 2 to 3, and p is 1; when the bond is absent, then when t is 0, q is 4 or more and p is 1, when t is 1 or more, q is 2 or more and p is 1;

followed by intramolecular amination to form (17) of the formula

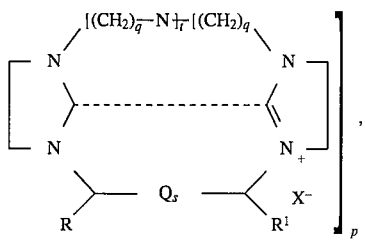

(17)

wherein the various terms are defined as for (16) and X is an anion, e.g., a halide ion; and then either basic or acidic hydrolysis to form a compound of Formula (I); or (B) an electrophlic substrate, in a polar solvent, optionally in the presence of a non-nucleophilic base, such as potassium carbonate to form (17) of the formula

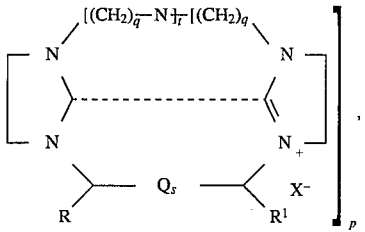

(17)

wherein Q, s, R and $R^1$ are defined as for Formula (I), X is an anion, and the dotted line represents the presence of a bond, t is 0, q is 2 to 3, and p is 1;

and then basic hydrolysis to form a compound of Formula (I); or (C) an electrophlic substrate, in a polar solvent, optionally in the presence of a non-nucleophilic base, such as potassium carbonate, to form (17) of the formula

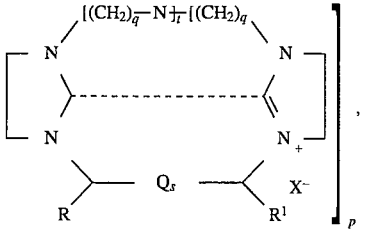

(17)

wherein Q, s, R and $R^1$ are defined as for Formula (I), X is an anion, and the dotted line represents the presence of a bond, t is 0, q is 2 to 3, and p is 1;

followed by prolonged heating in a polar solvent or by treatment with a peroxide solution to form (18) of the formula

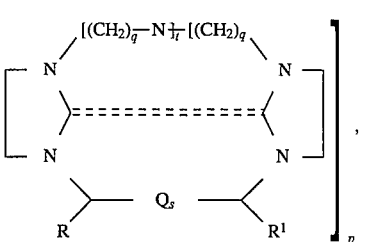

(18)

wherein Q, s, R and $R^1$ are defined as for Formula (I) and the dotted lines represent the presence of a double bond, t is 0, q is 2 to 3, and p is 1;

followed by basic hydrolysis to form the urea (19) of the formula

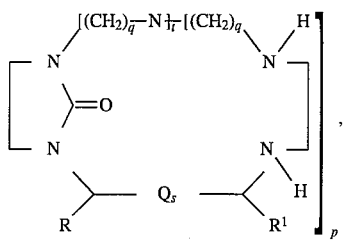

(19)

wherein Q, s, R and $R^1$ are defined as for Formula (I) and t is 0, q is 2 to 3, and p is 1;

and then basic hydrolysis under pressure to form a compound of Formula (I); and separating the desired polyazamacrocycle, i.e. by recrystalization from an aqueous basic solution.

In the present process to synthesize functionalized and nonfunctionalized polyazamacrocycles of Formula (I) from ethyleneamine derived imidazolines, for example, Cyclen (1,4,7,10-tetraazacyclododecane) was prepared by initially alkylating 1,1'-(1,2-ethanediyl)-bis[4,5-dihydro-1H]-imidazole (derived from TETA) with an appropriate electrophilic substrate, followed by base hydrolysis to provide the desired Cyclen of Formula (I). Application of this chemistry can be utilized to synthesize polyazamacrocycles of Formula (I) by the following general methods.

DETAILED DESCRIPTION OF THE INVENTION

Various terms used in the present application are defined as follows.

"acidic hydrolysis" means standard hydrolysis conditions in an aqueous system at a pH below about 6.5; for example acetic acid, phosphoric acid, HCl, HBr or $H_2SO_4$ (usually from 10 to 20 eqs), usually at an elevated temperature, e.g., a temperature from about 50° to about 120° C., preferably from about 80° to about 120° C.

"$C_1$–$C_6$ alkyl" means straight and branched chained alkyl such as methyl, ethyl, propyl, iso-propyl, tert-butyl (t-butyl), n-hexyl, and includes $C_1$–$C_4$ alkyl.

"alkylenepolyamine" means $C_2$–$C_{18}$ alkylene $N_2$–$N_6$ polyamine, preferred are $C_2$–$C_{10}$ alkylene $N_2$–$N_4$ polyamine, more preferred are $C_6$ alkylene $N_4$ polyamine; for example EDA, triethylenetetraamine (TETA), N,N'-bis(2-aminoethyl)-1,3-propanediamine, N,N'-bis(3-aminopropyl)-ethylenediamine, diethylenetriamine (DETA), pentaethylenehexaamine or tetraethylenepentaamine.

"ambient temperature" means room temperature or a temperature from about 20° to 26° C.

"aprotic solvent" means a non-nucleophilic solvent having a boiling point range above ambient temperature, preferably from about 25° to about 190° C., more preferably from about 80° to about 160° C., most preferably from about 80° to 150° C., at atmospheric pressure. Examples of such solvents are acetonitrile, DMF, diglyme, THF or DMSO.

"basic hydrolysis" means standard hydrolysis conditions in an aqueous system, at a pH above about 7.5; for example aqueous NaOH or KOH (usually from 3 to 20 eqs), usually at a temperature from about 0° to about 200° C., preferably from about 25° to about 105° C.; with process steps (A) and (B) described above preferably from about 90° to about 100° C.; with process step (C) above to urea (19) at about ambient temperature, preferably from about 25° to about 100° C.

"basic hydrolysis under pressure" means the use of a presure vessel (such as an autoclave at about 120 psi or a Paar bomb) under the other conditions for basic hydrolysis as defined above, such that the temperature for the hydrolysis is maintained at an elevated temperature, e.g., from about 150° to about 210° C., preferably from about 190° to 210° C.

"DETA" means diethylenetriamine.

"diglyme" means 2-methoxy ethyl ether.

"DMF" means N,N-dimethylformamide.

"EDB" means ethylenedibromide or 1,2-dibromoethane.

"EDC" means ethylenedichloride or 1,2-dichloroethane.

"electrophilic substrate" means an organic compound having 1 or 2 electrophilic centers (on carbon atoms) where nucleophilic agents (an amine; primary, secondary or tertiary) can react and contains the R, $R^1$ and X terms. Examples of such electrophilic carbon centers for substrates are vicinal substrates such as where the $C_2$-$C_4$ alkylidine is substituted with at least two electrophilic groups selected from halogen (Cl, Br, I), sulfonates such as toluene sulfonate, methane sulfonate or trifluoromethane sulfonate, epihalohydrin such as epichlorohydrin or epibromohydrin, 1,3-dihaloacetone such as 1,3-dichloroacetone, oxides such as ethylene oxide or ethylene carbonate, or tosylates, mesylates or triflates of ethylene glycol. Preferred compounds as the substrate include $C_2$-$C_4$ alkylidine (e.g. the 1,1- or 1,2-ethylidine or ethylene oxide) substituted with two dielectrophlic moieties (e.g. dibromo or dichloro groups), such as 1,2-dibromoethylidine.

"elevated temperature" means a temperature above ambient temperature, e.g., from about 30° to about 150° C., preferably from about 60° to about 125° C.

"EO" means ethylene oxide.

"formyl equivalent" means any compound capable of behaving like a formyl moiety [—C(O)—H] under the described process conditions, examples of such compounds are DMF, formic acid, formic acid esters, N,N-dimethylformamidedialkylacetals, trialkylorthoformates, bromoform, chloroform, iodoform, N,N-dialkyl formamides or trihalomethyl acetaldehyde. The "dialkyl" term includes $C_1$-$C_6$ alkyl groups that are either straight or branched chained alkyl groups. Preferred formyl equivalent compounds are DMF and di($C_1$-$C_6$ alkyl)acetals.

"intramolecular amination" means formation of a carbon to nitrogen bond where the carbon and nitrogen are in the same molecule [i.e., J. March, *Advanced Organic Chemistry*, 3rd ed., John Wieley & Sons, (1985 ), p 423].

"non-aqueous solvent" means any organic solvent containing less than 3% water, such as DMF, diglyme, and acetonitrile.

"non-nucleophilic base" means a base which does not act as a nuceolphile in the reactions with the reagents or compounds of this invention; for example, alkali metal carbonates such as potassium carbonate, cesium carbonate, sodium carbonate, or bicarbonates such as sodium bicarbonate. A preferred base is potassium carbonate.

"PEHA" means a mixture of pentaethylenehexaamine isomers containing greater than 30% of the linear isomer.

"peroxide solution" means dilute (about 1–10% w/w) aqueous hydrogen peroxide or aqueous peracids, such as peracetic acid, or derivatives which are capable of releasing peroxide under the reaction conditions, e.g., 10% aqueous $H_2O_2$.

"polar solvent" means a solvent which has a dipole moment ($\epsilon$) of 2.9 or greater, such as DMF, THF, ethylene gylcol dimethyl ether, DMSO, acetone, acetonitrile, methanol, ethanol, isopropanol, n-propanol, t-butanol or 2-methoxyethyl ether. Preferred solvents are DMF, diglyme, and acetonitrile.

"polar, aprotic solvent" means a polar solvent as defined above which has no available hydrogens to enchange with the compounds of this invention during reaction, for example DMF, acetonitrile, diglyme, DMSO, or THF.

"polyazamacrocycle" means a macrocyclic ring having from 3 to 6 nitrogens present in the backbone of the ring, the other members of the ring are carbon, oxygen, sulfur and silicon, but are preferably carbon.

"prolonged heating" means maintaining a temperature range of from about 80° to about 200° C. for from about 4 to about 48 hours.

"TEPA" means a mixture of tetraethylenepentaamine isomers containing greater than 40% of the linear isomer.

"TETA" means a mixture of triethylenetetraamine isomers containing greater than 50% of the linear isomer which is triethylenetetraamine, (7), and has the structure

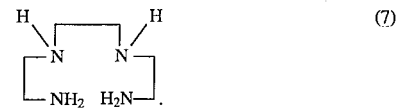

The following compounds and formulas are defined:

"Cyelen" means 1,4,7,10-tetraazacyclododecane, (6), a compound of Formula (I), and has the structure

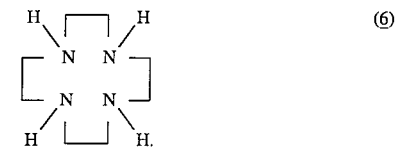

"EDA" means ethylenediamine, (8), and has the structure

"1,1'-(1,2-ethanediyl)-bis[4,5-dihydro-1H]-imidazole", (9a), and has the structure

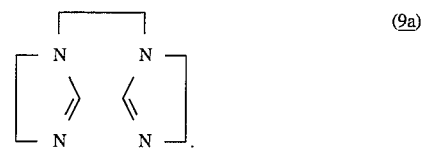

"1,2-ethanyl-2-[4,5-dihydro-1H]-imidazole", (10), and has the structure

"DETA" means diethylenetriamine, (1), and has the structure

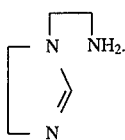
(1)

"TEPA" means tetraethylenepentaamine, (11), and has the structure

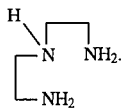
(11)

"1,1'-(2,2'-diethylamine)-bis[4,5-dihydro-1H]-imidazole", (12), and has the structure

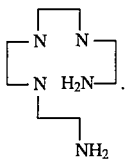
(12)

"PEHA" means pentaethylenehexaamine, (13), and has the structure

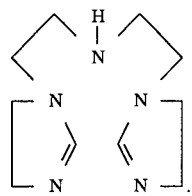
(13)

"1,2-ethanediyl-bis(1,2-ethanyl-2-[4,5-dihydro-1H]-imidazole), (14), and has the structure

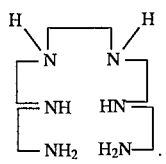
(14)

The present invention for preparing the compounds of Formula (I) utilizes imidazolines as the key, critical substrate prior to the formation of the polyazamacrocycle of Formula (I). The reason that these imidazolines are well suited for this chemistry is twofold: once formed, the nitrogen bearing the double bond experiences enhanced nucleophilicity. This attribute is a direct result of the lone pair of electrons found on the adjacent nitrogen (note the resonance structure possible of the bis-imidazoline derived from TETA). Secondly, the secondary amines of the starting TETA (7) are now protected from reacting with the electrophilic substrate.

The approach of the present invention taken towards the synthesis of this class of polyazamacrocyclic compounds of Formula (I), reported herein, is the reaction of an imidazoline (9) with an electrophilic substrate. These imadazolines (9) are prepared by reaction of an alkylenepolyamine with a formyl equivalent, (i.e., N,N-dimethylformamide dimethoxy acetal) which yields the imidazoline (9) upon heating (about 50° to about 100° C.) either neat or in an organic solvent (e.g., toluene, diglyme, xylene, DMF, THF, acetonitrile, 1,4-dioxane, diethyl ether, hexane, heptane or octane). The by-products from this formamide acetal reagent are the appropriate alcohol (i.e., $CH_3OH$) and dimethylamine.

After cyclization, removal of the protecting groups on the secondary amines (e.g., Scheme II) is easily performed by base hydrolysis. Thus, the use of expensive protecting groups, harsh deprotection conditions, and the expensive disposal of by-product salts from the prior art procedures can be avoided. As a result, the number of manipulations required to synthesize polyazamacrocycles by the process of this invention (vs the conventional azamacrocycle sysnthesis) is minimal.

Generation of the imidazolines can be performed a variety of ways, e.g., by treating the appropriate $C_2$–$C_6$ alkyleneamine (i.e., ethyleneamine ) with a formyl equivalent [such as DMF under autoclave conditions (t=>150° C.)].

Treatment of the resulting imidazoline (9) with a electrophilic substrate yields a polyazamacrocycle intermediate, i.e. (17). With, for example, use of a electrophilic substrate, it is believed that the nucleophilic imidazoline nitrogens displace the electrophilic moieties directly to yield, for example, (17). Upon basic hydrolysis, for example, of (17) yields the polyazamacrocycle compound of Formula (I), for example Cyclen (6). When this approach is taken, no appreciable by-products are noted. Only the polyazamacrocycle of Formula (I) and recovered starting material alkylenepolyamine are isolated.

With the use of ethylene oxide, once again the nucleophilic imidazoline nitrogen opens the ethylene oxide to yield (16). Intramolecular amination of (16) yields (17) which is then hydroyzed under basic conditions to provide Cyclen, (6).

While not wishing to be bound by theory, it is believed that the advantageous results of the present invention are obtained because of intramolecular reactions as shown in the following Schemes. Schemes I, II and I are representative of the compounds of Formula (I) and although directed to only one group of such compounds can be used to prepare the other groups within Formula (I).

Scheme I
Preparation of Nucleophilic Intermediates

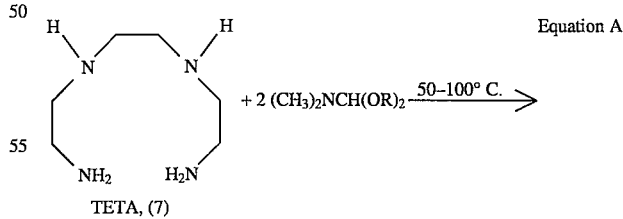

TETA, (7)

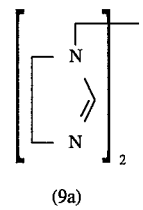

(9a)

Scheme I
Preparation of Nucleophilic Intermediates
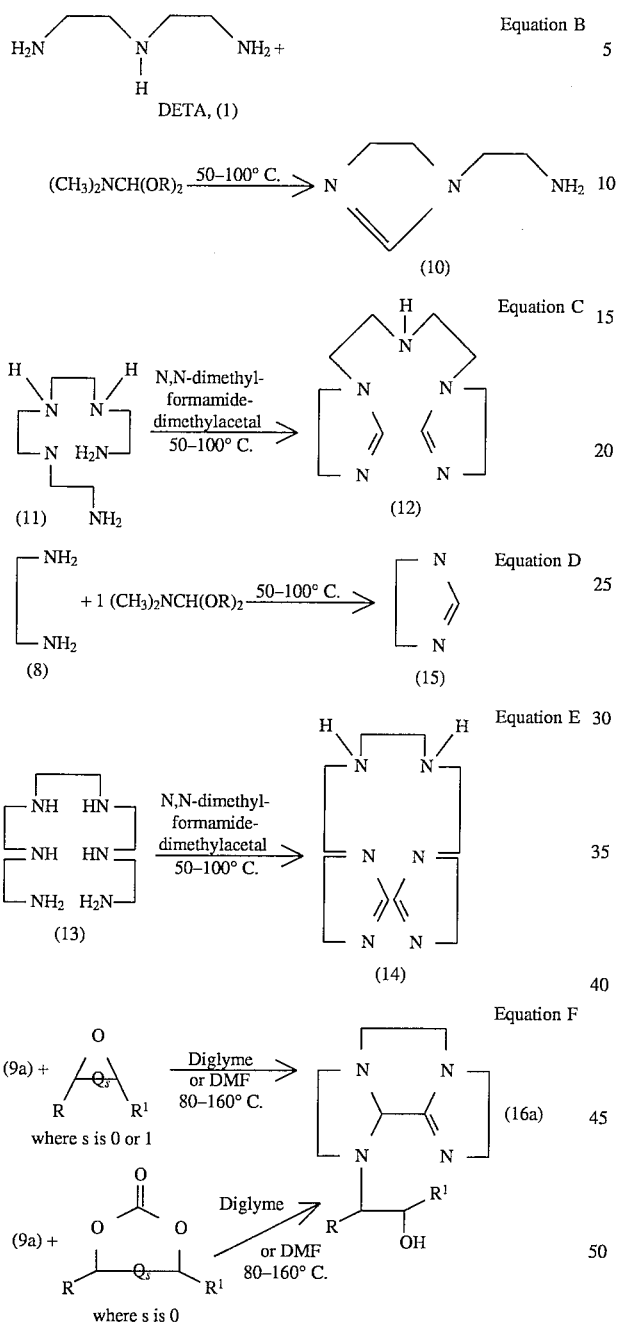
Scheme II
Preparation of Azamacrocycles Containing 3–6 Nitrogens
(16a) $\xrightarrow[\text{2) reflux, aqueous}]{\text{1) intramolecular amination}}$  Equation A
NaOH (5–10 eq)
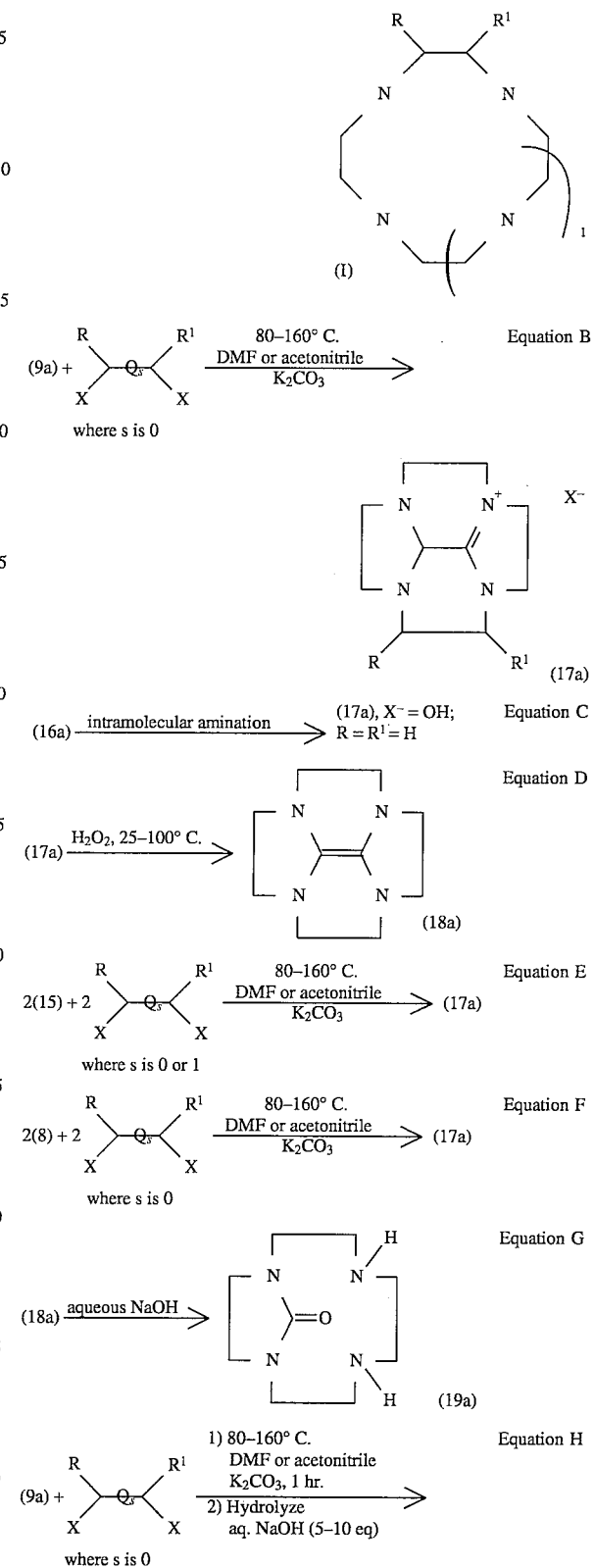

-continued
Scheme II
Preparation of Azamacrocycles Containing 3-6 Nitrogens
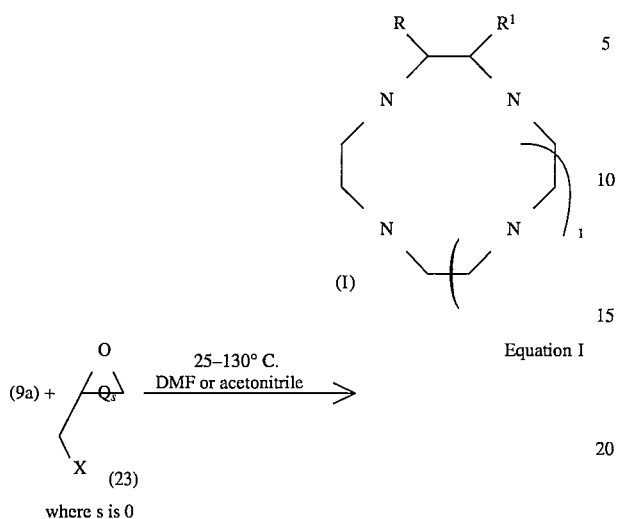
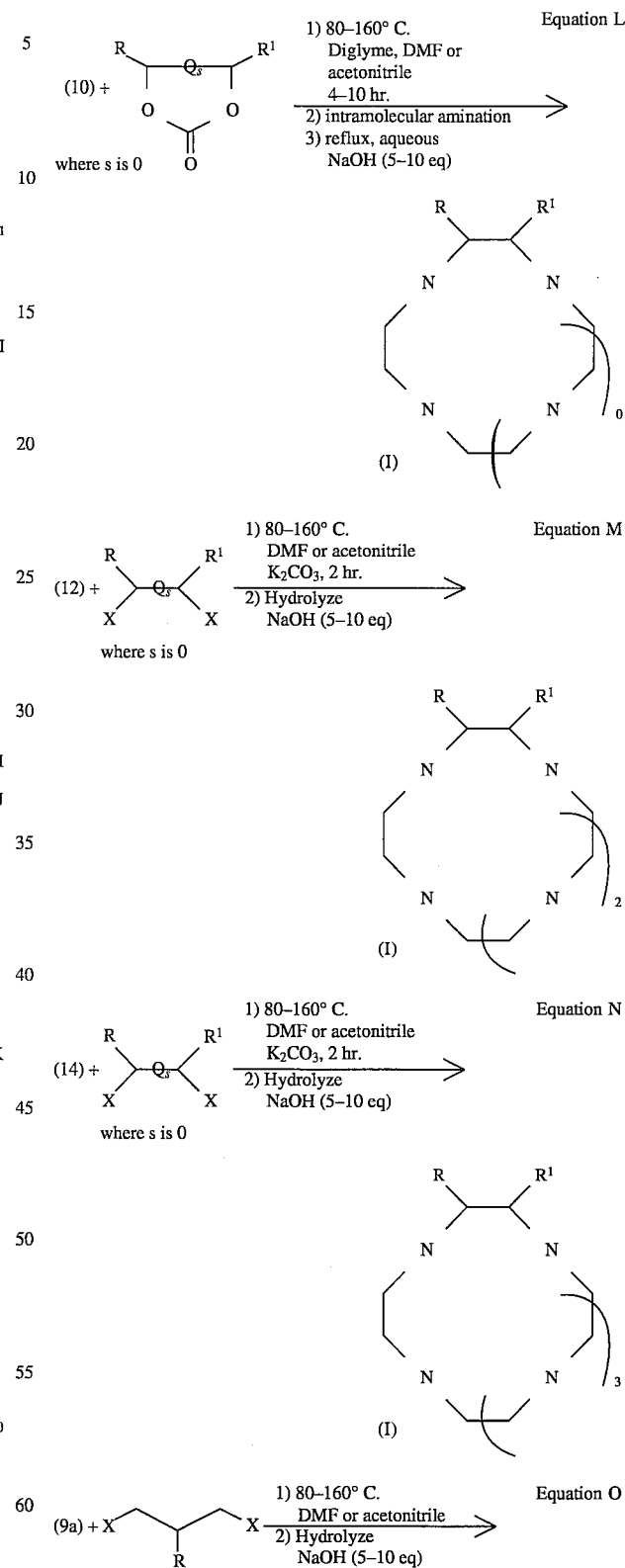

-continued
Scheme II
Preparation of Azamacrocycles Containing 3–6 Nitrogens

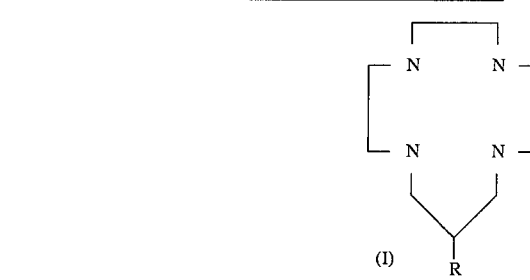

Scheme III
Preparation of Pure TETA

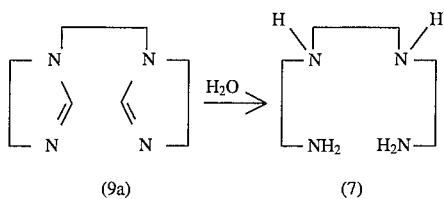

When the polyazamacrocycle of Formula has Q equal to —C(O)—, the compounds are generally prepared as in Scheme IV below. Although only one group of compounds of Formula (I) is shown in this Scheme IV, the other groups of compounds of Formula (I) can be prepared in a similar manner.

Scheme IV

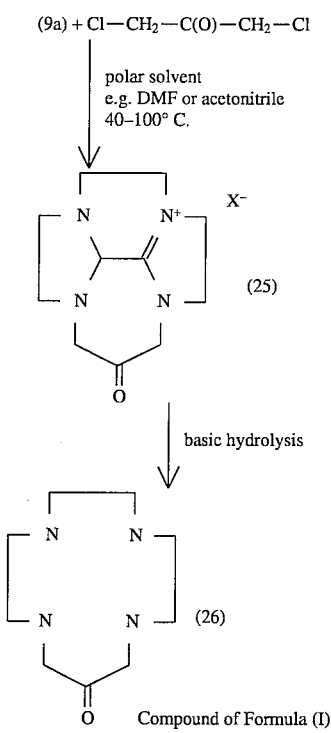

Compound of Formula (I)

In the above Schemes the various terms are defined as For Formula (I) above.

DETAILED DESCRIPTION OF SCHEMES I AND II

In the above Schemes, the general process description illustrates specific steps that may be used to accomplish a desired reaction step. The general description of these process steps follows.

Synthetic Scheme I above depicts the synthesis of the starting materials and begins with the formation of the imidazolines (9a), (10), (12), (14) and (15). The appropriate alkyleneamine [i.e., triethylenetetraamine for (9a), diethylenetriamine for (10), TEPA for (12), PEHA for (14) and ethylenediamine for (15)] is either dissolved in a solvent [e.g., toluene, benzene, hexane, diglyme, diethyl ether, THF, acetonitrile, dimethylformamide (DMF)] or reacted neat with the next reagent. The N,N-dimethylformamide dimethyl acetal [2 equivalents (eqs)] is added to the solution at room temperature. The solution is then heated at about 50° to about 110° C., preferably from about 60° to 100° C. (Equation A–D). After 15–30 minutes (mins) at an elevated temperature, the heat is removed and the solution is allowed to reach room temperature (about 20° to about 25° C.). The solvent, if present, is then removed by vacuum distillation. The resulting imidazolines can be purified using standard procedures, such as through recrystallization or distillation.

Other methodologies for the synthesis of imidazolines known to those skilled in the art also could be utilized. For example, the condensation of formyl equivalents under reaction conditions in the Scheme II will also yield the imidazolines.

Further treatment of (9) with 1 eq of ethylene oxide (or ethylene carbonate which is an ethylene oxide equivalent) in a polar, aprotic solvent (e.g., DMF, diglyme) at 120°–160° C. for 4–10 hours (hrs) yields (16a) (Equation E). No further purification is performed.

In Scheme II, polyazamacrocyclic compounds are prepared using: polar, aprotic solvents, such as those outlined for Scheme I, (e.g., DMF, diglyme, acetonitrile); the compounds of (9a), (10), (12), (14) or (15) as the nucleophilic species; and an ethylene oxide or an ethylene carbonate as the electophilic substrate. This method results in the formation of an intermediate [i.e., (16a) Scheme I, Equation E]. Intramolecular amination of this intermediate results in the formation of a polyazamacrocycle, i.e. Scheme II, Equation C, (17a). Hydrolysis of this intermediate, i.e. (17a), with 3–15 eq of aqueous NaOH yields the "free" polyazamacrocycle (Equations A, H, J, K, L, M, N and O).

Using a vicinal 1,2-dihalo substrate as the electrophilic substrate in forming the polyazamacrocycle is accomplished, for example, by treating (9) with 1,2-dibromoethane (or 1,2-dichloroethane) in a polar solvent, in the presence of non-nucleophilic base (Equation B). After 0.5–5 hrs at about 60°–120° C., the solvent is removed by distillation yielding a polyazamacrocycle intermediate, i.e. (17), which is hydrolyzed in 3–8 eq of refluxing aqueous NaOH (10–50% w/w), yielding the free polyazamacrocyclic (Equations G, H, J, K, L and M) amine of Formula (I). The resulting tetraazamacrocycle is isolated by standard procedures, i.e. recrystalization from an aqueous basic solution.

The preferred order of addition for the synthesis of (17) involves adding a DMF or acetonitrile solution containing EDB and (9) at room temperature to a heated solution of $K_2CO_3$ in DMF or acetonitrile. The hydroysis is then conducted as described before. The advantage of this modification is that a higher conversion of (9) to (17) is achieved. Although not as desireable, all reactants can be combined at one time in DMF or acetonitrile and then heated.

Alternatively, (17) can be converted to (18) either by prolonged heating or by treatment with a peroxide solution (Equation D). Conversion of (18a) to (19a) is accomplished by treatment under basic hydrolysis conditions (Equation G). Cyclen (6) is formed from (19a) by basic hydrolysis under pressure.

DETAILED DESCRIPTION OF SCHEME IV

In Scheme IV the cyclized ketone intermediate (25) is prepared by simultaneous additions of 1,3-dichloroacetone and (9a) to an acetonitrile/$K_2CO_3$ slurry. The resulting cyclized product can then be hydrolyzed under basic hydrolysis conditions to provide (26).

The synthesis of dialkyl derivatives of 1,1'-(1,2-ethanediyl)-bis[4,5-dihydro-1H]-imidazole is reported [*Chem. Abst.* 100(13):102774f (Romanian Patent, RO 79987 B, 30 Sep. 1982); *Chem. Abst.*:2456a Belgian Patent 613, 063, 15 Feb. 1962 to Armour & Co.] by treating TETA with a long chain fatty acid at high temperatures. The present invention provides the first obtaining of an unsubstituted 1,1'-(1,2-ethanediyl)-bis[4,5-dihydro-1H]-imidazole (9a) from the quantative reaction of TETA and N,N-dimethylformamide dialkyl acetals.

All other starting materials are either purchased commercially or made by known processes.

The polyazamacrocycles of Formula (I) prepared by the process of this invention are important as intermediates for making derivatives useful in various medical applications, such as magnetic resonance imaging (diagnostic) where a derivative of Cyclen with $Gd^{+3}$ is used, e.g. the hydrogens of Cyclen (N—H) are replaced with methylenecarboxylates (e.g., 1,4,7,10-tetraazacyclododecane-1,4,7,10-tetraacetic acid (DOTA), U.S. Pat. No. 4,639,365); therapeutic nuclear medicine where 1,4,7,10-tetraazacyclododecane-1,4,7,10-tetramethylenephosphonic acid (DOTMP) is complexed with rare earth nuclides for delivery of the nuclide to bone for relief of bone pain, tumor regression or bone marrow supression (e.g., U.S. Pat. No. 4,976,950); in antibody (e.g. monoclonal antibodies) delivery systems as a chelate for the metal ion [*J. Am. Chem. Soc.* 110, 6266–6267 (1988)]; and in in vivo and in vitro delivery systems for diagnosis or therapy applications.

Also the present polyazamacrocycles of Formula (I) are chelants capable of forming chelates when used for water treatment. These polyazamacrocycles can also be used as a non-hypochlorite bleach (e.g., see European 0 458 397).

The invention will be further clarified by a consideration of the following examples, which are intended to be purely exemplary of the present invention.

GENERAL EXPERIMENTAL

The reactions were analyzed by gas chromatography (GC) on a HP-5890A instrument. The column employed was a HP-Ultra-1, 50 m×33 m. The temperature program was: Initial Temp. 60° C. for 10 min, the rate of temperature increase was 10° C./min up to 270° C. The final temperature was held for 15 min.

All percentages are in weight percent unless stated otherwise.

TETA was obtained from The Dow Chemical Company's ethyleneamine TETA isomer stream.

All other reaction reagents were obtained from commercial suppliers and used as received without further purification or purified prior to use.

NMR spectra were recorded on a Bruker AC-250 MHz spectrometer equipped with multi-nuclear quad probe ($^1H$ and $^{13}C$) at 297° K. unless otherwise indicated and measured as parts per million (ppm).

PREPARATION OF STARTING MATERIALS

EXAMPLE A

Preparation of 1,2-Ethanyl-2-[4,5-dihydro-1H]-imidazoline, (10).

To a stirring solution of 1.0 g (0.0097 mol) of diethylenetriamine (DETA) was added in one portion, 1.25 g (0.0097 mol) of N,N-dimethylformamide dimethyl acetal, at 20° to 25° C. The solution was then brought to reflux (60°–65° C.). The cooled solution was stripped of methanol and dimethylamine via rotoevaporation leaving a light yellow oil. Further distillation of the oil provided 0.84 g, yield of 73%, of the desired product, which is represented by the formula:

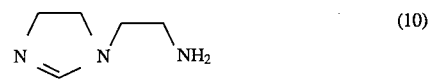 (10)

EXAMPLE B

Preparation of 1,1'-(1,2-Ethanediyl)-bis[4,5-dihydro-1H]-imidazoline, (9a), using a solvent.

To a stirring solution of 500 mL of toluene and linear TETA (100 g, 0.68 mol) was added 94% pure N,N-dimethylformamide dimethyl acetal (173.37 g, 1.36 mol). The solution was refluxed for 30 min. The toluene was removed via rotovap. The resulting light yellow solid which was filtered and rinsed with THF. The resulting white solid was isolated in 92% yield (104 g, 0.63 mole), mp 107–9 C. and further characterized by:

$^1H$ NMR (CDCl$_3$) δ6.7 (s, 2H), 3.7 (t, 4H), 3.1–3.2 (overlapping signals, 8H);

$^{13}C$ NMR (CDCl$_3$) δ157.2 (CH), 55.0 (CH$_2$), 48.4 (CH$_2$), 46.4 (CH$_2$); and Mass Spec m/e 167 (M+1, 1), 166 (6, 83 (100), 56 (89).

The product is represented by the formula:

 (9a)

EXAMPLE C

Preparation of 1,1'-(1,2-Ethanediyl)-bis[4,5-dihydro-1H]-imidazoline (9a) from TETA, without a solvent.

A: Preparation of 1,1'-(1,2-Ethanediyl)-bis[4,5-dihydro-1H]-imidazole (9a) from TETA The TETA (253 g, 1.73 mol) was added to 94% pure N,N-dimethylformamide dimethyl acetal (307.03 g, 2.42 mol). As the solution was warmed to 65° C. with stirring, methanol was liberated. The solution was heated for 20 min at 65° C. The methanol and dimethylamine were stripped using a rotoevaporator. The bis-imidazoline was crystallized from the oil by treating the oil with a 50:50 (v/v) mixture of ethylacetate and cyclohexane. The resulting precipitate was filtered. The filtrate was reconcentrated and the above procedure repeated until no more bis-imidazloine precipitated from solution. The overall yield of the bis-imidazoline (9a) was 133 g (66% based the DMF acetal). The product is represented by the formula:

$$\left[\begin{array}{c}\left[\begin{array}{c}-N\\ \rangle\!\!\!\!/\\ -N\end{array}\right]\end{array}\right]_2 \quad (9a)$$

B: Preparation of cyclized intermediate (17a)

To a vigorously stirring mixture of $K_2CO_3$ (0.72 mol) in 1 L of DMF at 100° C. was added a 1.3 L DMF solution containing both (9) (104 g, 0.63 mol) and 1,2-dibromoethane (165 g, 0.88 mol). Upon completion of the addition (~30 min), the resulting solution was heated for an additional 30 min at 100° C. After cooling to 50° C., the $K_2CO_3$ was filtered and the resulting filtrate was concentrated to dryness. The crude cyclized salt was washed with acetone to remove the trace impurities. The isolated yield of (17a) was 99% (171 g, 0.62 mol) and characterized by:

$^{13}C$ NMR (CDCl$_3$) δ162.0 (C), 72.7 (CH), 54.2 (CH$_2$), 52.4 (CH$_2$), 45.5 (CH$_2$), 44.3 (CH$_2$).

The product is represented by the formula:

$$\left[\begin{array}{cc}-N & N^+-\\ \rangle\!\!\!\!=\!\!\!\!/\\ -N & N-\end{array}\right] \quad X^- \quad (17a)$$

EXAMPLE D

Preparation of (18a)

The procedure used for the synthesis of (17a) was followed using 1.14 g (6.8 mmol) of (9) except that the DMF solution was heated for 12–14 hours at 100° C. The cooled solution was stripped to dryness leaving an amber colored solid. No further purification of the material was performed. The compound is characterized by:

$^1H$ NMR (D$_2$O) δ4.3 (s), 4.0 (s); and $^{13}C$ NMR (D$_2$O) δ46.3 (CH$_2$), 54.3 (CH$_2$), 150.6 (C).

The product is represented by the formula:

$$\left[\begin{array}{cc}-N & N-\\ \rangle\!\!\!\!=\!\!\!\!/\\ -N & N-\end{array}\right] \quad (18a)$$

EXAMPLE E

Preparation of (18a) via Hydrogen Peroxide

The cyclized intermediate, (17a), (1 g, 3.6 mmol) was dissolved in 10 mL of water. A 10% $H_2O_2$ was added to the solution. The solution was heated to reflux. After 30 min, the heat source was removed and the solution was carefully stripped to dryness. No further purification of the material was performed. The product is represented by the formula:

$$\left[\begin{array}{cc}-N & N-\\ \rangle\!\!\!\!=\!\!\!\!/\\ -N & N-\end{array}\right] \quad (18a)$$

EXAMPLE F

Preparation of 4,5-Dihydro-1H-imadazole, (15)

EDA (50 g, 0.83 mol) and DMF-dimethoxy acetal (52.8 g, 0.42 mol) were placed into a round bottom flask and warmed to 65°–70° C. After 30 min. the heat source was removed and the methanol and dimethylamine were removed by rotoevaporation. The excess EDA was then removed by distillation. Final purification of 4,5-dihydro-1H-imidazole was achieved by distillation (62°–64° C., 2 mm Hg). The isolated material was obtained in a yield of 20.5 g (70%) and is represented by the formula:

$$\left[\begin{array}{c}-N\\ \rangle\!\!\!\!/\\ -N\end{array}\right] \quad (15)$$

EXAMPLE G

Preparation of 1,1'-(1,2-ethanediyl)-bis[4,5-dihydro-1H]-imidazoline, (9a)

4,5-Dihydro-1H-imadazole (0.5 g, 7.1 mmol), prepared in Example F, 1.48 g (11 mmol) of $K_2CO_3$, and 10 mL of DMF were placed in a round bottom flask, under nirogen. The mixture was heated to 90° C., then a solution of 0.67 g (3.57 mmol) of EDB in 5 mL of DMF was added dropwise over 20 min. Heating was continued for an additional 30 min. The $K_2CO_3$ was filtered from the solution and the resulting filtrate was concentrated to dryness. The resulting off white semi-solid was recrystallized from THF to yield 0.45 g (75%) of the title product and is represented by the formula:

$$\begin{array}{c}/\!\!\!\!\!-\!\!\!\!\!\backslash\quad/\!\!\!\!\!-\!\!\!\!\!\backslash\\ N\diagdown\diagup N\quad N\diagdown\diagup N\end{array} \quad (9a)$$

EXAMPLE H

Preparation of a cyclized intermediate, (17a)

The 4,5-dihydro-1H-imidazole (0.5 g, 7.1 mmol), prepared in Example G, and 1.8 g (9.6 mmol) of EDB were dissolved in 10 mL of DMF. This solution was then added drpwiseover about 20 min. to a stirring solution of DMF/ $K_2CO_3$ which was at 90°–100° C. Heating was continued fo an additional 1 hour. The $K_2CO_3$ was then removed by filteration and the resulting filtrate was concentrated to dryness. The resulting semisolid was rinsed with acetone to yield (17a) as represented by the following formula:

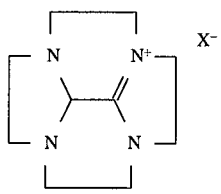

(17a)

EXAMPLE I

Preparation of cyclized intermediates, (25)

The imidazole (9a) (5 g, 30 mmol) and 4.2 g (33 mmol) of 1,3-dichloroacetone were dissolved in separate 50 mL aliquots of acetonitrile. These solutions were then added simultaneously to a slurry of 5 g of $K_2CO_3$ in 50 mL acetonitrile over a 10 min period at 25° C. After addition was completed, the solution was filtered and concentrated in vacuo to give, as a brown semi-solid, (25), as represented by the following formula:

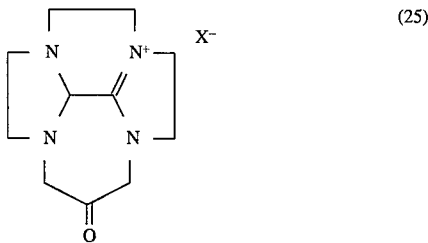

(25)

PREPARATION OF FINAL PRODUCTS

EXAMPLE 1

Preparation of Cyclen (6)

The cyclized intermediate [(17a), 113 g, 0.41 mol], prepared by the procedure of Example C, Part B, was dissolved in water to give a total volume of 450 mL and was added dropwise to a refluxing solution of 400 mL of NaOH (8 eq, 129 g, 3.3 mol). The solution was heated for an additional 30 min after completion of the addition of the cyclized intermediate. The aqueous caustic solution was filtered while hot and then the filtrate cooled to room temperature. The aqueous filtrate was then concentrated (rotoevaporator) until crystalline solid was observed in the solution. After cooling, Cyclen was filtered and the process was repeated on the filtrate until no further crystallization occurred. The aqueous solution was then concentrated to dryness and the remaining precipitate removed by extractions of the solid residue with hot toluene. The overall yield of (6) was 88% (62 g, 0.36 mol) and characterized by:

$^1$H NMR (CDCl$_3$) δ2.54;

$^{13}$C NMR (CDCl$_3$) δ45.9; and

Mass Spec m/e 173 (M+1), 173 (2), 128 (8), 104 (45), 85 (100), 56 (80).

The product is represented by the formula:

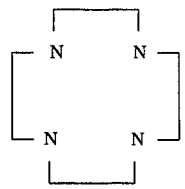

(6)

EXAMPLE 2

Preparation of (19a)

The cyclized intermediate (18a) (1 g, 5.2 mmol), prepared by the procedure of Example D, was dissolved in 15 mL of water. The aqueous solution was added dropwise to refluxing solution of NaOH (5 eq, 1.04 g, 25 mmol). After being heated for 60 min, the solution was cooled to room temperature and extracted with chloroform (4×20 mL). The resulting chloroform solution was dried over $K_2CO_3$, filtered and stripped to dryness. The resulting solid was not purified and characterized by:

$^1$H NMR (CDCl$_3$) δ2.4 (br s, 2 NH), 2.6 (m, 2H), 2.9 (m, 6H), 3.1 (m, 2H), 3.6 (m, 4H), 4.0 (m, 2H);

$^{13}$C NMR (CDCl$_3$) δ42.0 (CH$_2$), 44.9 (CH$_2$), 45.8 (CH$_2$), 49.6 (CH$_2$), 165.9 (C);

IR (CHCl$_3$) 2998, 2932, 2895, 1675, 1496, 1455, 1265 cm$^{-1}$; and

Mass Spec m/e 199 (M+1, 2), 198 (12), 155 (100), 142 (37), 126 (18), 113 (53), 99 (33), 85 (45), 70 (25), 56 (73).

The product is represented by the formula:

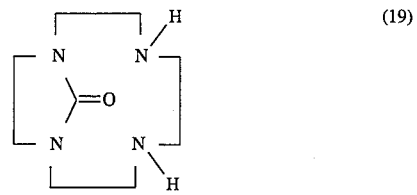

(19)

EXAMPLE 3

Preparation of (16a)

The bis-imidazoline (9a) (1.12 g, 6.8 mmol), prepared by the procedure of Example B, and the ethylene carbonate (0.6 g, 6.8 mmol) were dissolved in 50 mL of anhydrous DMF. The resulting solution was heated to 140° C. for 5 hours. The heat source was removed and the resulting solution was stripped to dryness. No further purification on the material was performed. The product is characterized by:

$^{13}$C NMR (CDCl$_3$) δ42.9 (CH$_2$), 44.9 (CH$_2$), 48.4 (CH$_2$), 50.6 (CH$_2$), 51.4 (CH$_2$), 52.7 (CH$_2$), 58.3 (CH$_2$), 60.1 (CH$_2$), 75.1 (CH), 165.6 (C); and Mass Spec m/e 211 (M+1) (3), 210 (21), 180 (32), 138 (100), 124 (26), 97 (25), 83 (12), 56 (31).

The product is represented by the formula:

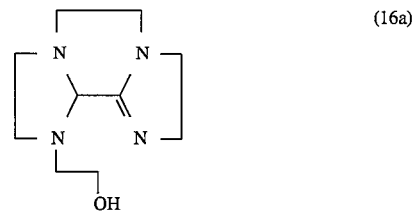

(16a)

EXAMPLE 4

Preparation of Cyclen, (6) in n-propanol

When the procedure of Example C, Part B, was repeated by adding an n-propanol solution containing 0.52 mL (6 mmol) of EDB and 4.5 mmol of (9a), prepared by the procedure of Example C, Part A, to a solution of 70 mL of refluxing anhydrous n-propanol containing 0.62 g of K₂CO₃ and refluxed for 18 hrs, after removal of the solvent an amber residue remained which was dissolved in water and analyzed by $^{13}$C NMR to indicate that the major product was (17a). Basic hydrolysis of (17a) provided a 55% yield of (6) which was identical to that obtained using DMF in Example 1. The product is represented by the formula:

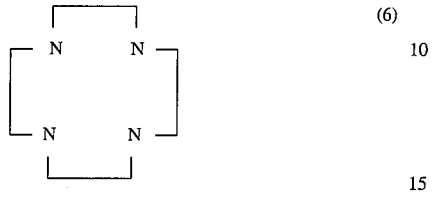
(6)

EXAMPLE 5

Preparation of Cyclen, (6) in ethylene glycol dimethyl ether

When the procedure of Example C, Part B, was repeated by adding an ethylene glycol dimethyl ether solution containing 0.52 mL (6 mmol) of EDB and 4.5 mmol of (9a) prepared by the procedure of Example C, Part A, to a solution of 70 mL of refluxing ethylene glycol dimethyl ether containing 0.62 g of K₂CO₃ and refluxed for 24 hrs, after removal of the solvent by decanting, an amber residue remained which was dissolved in water and analyzed by $^{13}$C NMR to indicate that the major product was (17a). Basic hydrolysis of (17a) provided a 50% yield (6) which was identical to that obtained using DMF in Example 1. The product is represented by the formula:

(6)

EXAMPLE 6

Preparation of Cyclen, (6) in acetonitrile

When the procedure of Example C, Part B, was repeated by adding a 60 mL acetonitrile solution containing 7.7 g (41 mmol) of EDB and 30 mmol of (9a), prepared by the procedure of Example C, Part A, to a solution of 61 mL of refluxing acetonitrile containing 4.0 g of K₂CO₃ and refluxed for 2 hrs, after removal of the solvent by decanting, an amber residue remained which was dissolved in water and analyzed by $^{13}$C NMR to indicate that the major product was (17a). Basic hydrolysis of (17a) provided a 85% yield and was identical to that obtained using DMF in Example 1. The product is represented by the formula:

(6)

EXAMPLE 7

Preparation of Cyclen, (6) in diglyme

When the procedure of Example C, Part B, was repeated by adding a diglyme solution containing 0.52 mL (6 mmol) of EDB and 4.5 mmol of (9a), prepared by the procedure of Example C, Part A, to a solution of 61 mL of refluxing diglyme containing 0.62 g of K₂CO₃ and refluxed for 9 hrs, after removal of the solvent by decanting, an amber residue remained which was dissolved in water and analyzed by $^{13}$C NMR to indicate that the major product was (17a). Basic hydrolysis of (17a) provided a 85% yield and was identical to that obtained using DMF in Example 1. The product is represented by the formula:

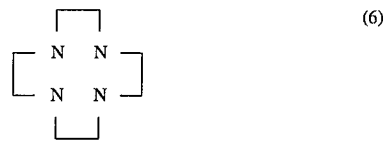
(6)

EXAMPLE 8

Preparation of 1,4,7-triazacyclononane in DMF

When the procedure of Example C, Part B, was repeated using (10), prepared by the procedure of Example A, and alkylating with a vicinal dihalogenated ethane (EDB or EDC), followed by basic hydrolysis, there was obtained a 1,4,7-triazacyclononane, which is represented by the following formula:

(22)

EXAMPLE 9

Preparation of 2,3-dicarboxyltetraazacyclododecane

When the procedure of Example C, Part B, was repeated using (9a), prepared by the procedure of Example C, and alkylating with 2,3-dibromosuccinic acid, there was obtained 2,3-dicarboxyltetraazacyclododecane, which is represented by the following formula:

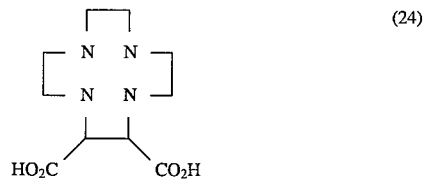
(24)

EXAMPLE 10

Preparation of Cyclen (6) from (19a).

The urea (19a), 0.5 g (2.53 mmol), was dissolved in 50 mL of water. To this solution was added equivalents of NaOH (0.8 g, 50% w/w solution). The solution was then placed in a 300 mL Paar bomb and heated with stirring to 200° C. After 3 hrs. the reaction was allowed to cool. The aqueous solution was then concentrated to the point of crystallization of Cyclen. The product was then filtered and dried to yield Cyclen (6), having the same characterization data as in Example 1. The product is represented by the formula:

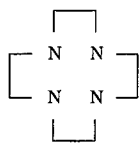

EXAMPLE 11

Preparation of (21a) from (9)

To a stirring mixture of DMF (10 mL) at 100° C. was added a 15 mL solution of DMF containing both 1 g (6.0 mmol) of the bis-imidazoline (9) and 0.9 g (6.54 mmol) of the epibromohydrin (23). Upon completion of the addition (about 15 min), the resulting solution was heated for an additional 45 min at 100° C. After cooling to 50° C. the solution was concentrated to dryness. The isolated yield of the crude intermediate (20a) as a racemic mixture was 1.78 g, 99%. The intermediate is characterized by:

$^{13}$C NMR (D$_2$O) δ166.0, 165.8, 67.5, 67.3, 62.5, 61.6, 54.9, 54.7, 54.0, 53.8, 53.2, 53.1, 52.8, 52.7, 48.5, 47.9, 45.2, 44.2.

The intermediate is represented by the formula:

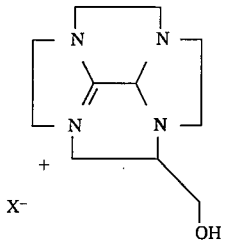

The intermediate (20a) was hydrolyzed by basic hydrolysis to the product (21a). No further purification on the material was performed. The product is represented by the formula:

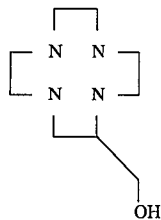

EXAMPLE 12

Preparation of (26) from (25)

The cyclized intermediate (25), prepared by the procedure of Example I, was dissolved in 20 mL of water, then 10 mL of 50% NaOH was added. The solution was heated to 90 for 1 hour, then cooled and concentrated in vacuo to give (26) as a viscous yellow oil which is represented by the formula:

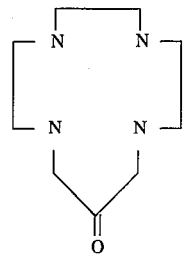

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter.

What is claimed is:

1. A process for preparing polyazamacrocycle compounds of the formula

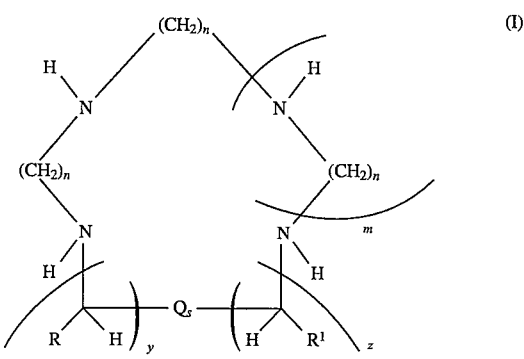

wherein:

each n is independently 2 or 3;

m is 0 or an integer from 1 to 3;

s is 0 or 1;

y is 0 or 1;

z is 0 or 1;

with the proviso that at least 2 of s, y, and z must be 1;

Q is —CH$_2$—, —C(O)— or —CHR;

R is hydrogen, C$_1$–C$_6$ alkyl, —CO$_2$H, —CO$_2$(C$_1$–C$_6$ alkyl) or phenyl;

R$^1$ is hydrogen, —CO$_2$H, —CO$_2$(C$_1$–C$_6$ alkyl), C$_1$–C$_6$ alkyl, C$_1$–C$_6$ alkyl substituted by NH$_2$, NO$_2$, isothiocyanato, semicarbazido, thiosemicarbazido, maleimido, bromoacetamido or OR$^2$, phenyl or phenyl substituted by NH$_2$, NO$_2$, isothiocyanato, semicarbazido, thiosemicarbazido, maleimido, bromoacetamido or OR$^2$; or R and R$^1$ can be taken together to form a phenyl or phenyl substituted by NH$_2$, NO$_2$, isothiocyanato, semicarbazido, thiosemicarbazido, maleimido, bromoacetamido or OR$^2$; and R$^2$ is hydrogen or C$_1$–C$_4$ alkyl;

which comprises reacting an alkylenepolyamine with a formyl equivalent, either neat or in a nonaqueous solvent, to form the unsubstituted imidazoline of the formula

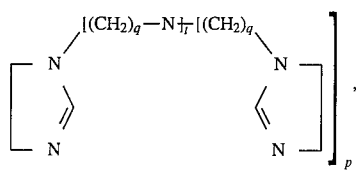 (9)

wherein
q is independently 2 or 3;
p is 0 or 1;
t is 0, 1 or 2; and
followed by reacting (9) with:
(A) 1 equivalent of an ethylene oxide or an ethylene carbonate, in an aprotic solvent, to form an alcohol (16) of the formula

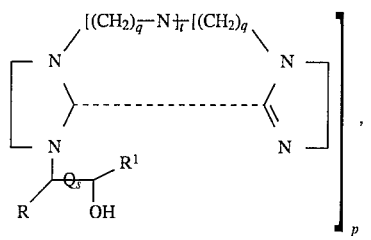 (16)

wherein Q, s, R and $R^1$ are defined as for Formula (I) and the dotted line represents the optional presence of a bond; when the bond is present, then t is 0, q is 2 to 3, and p is 1; when the bond is absent, then when t is 0, q is 4 or more and p is 1, when t is 1 or more, q is 2 or more and p is 1;

followed by intramolecular amination to yield (17) of the formula

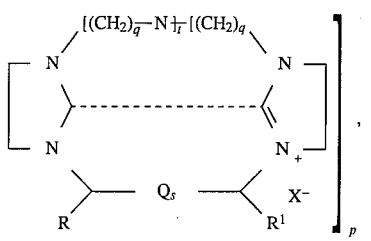 (17)

wherein the various terms are defined as for (16) and X is an anion, e.g., a halide ion;

and then either basic or acidic hydrolysis to form a compound of Formula (I); or
(B) an electrophlic substrate, in a polar solvent, optionally in the presence of a non-nucleophilic base, to form a salt (17)) of the formula

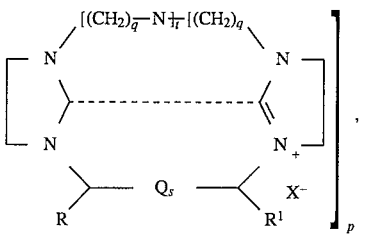 (17)

wherein Q, s, R and $R^1$ are defined as for Formula (I), X is an anion, and the dotted line represents the presence of a bond, t is 0, q is 2 to 3, and p is 1;

and then basic hydrolysis to form a compound of Formula (I); or
and then basic hydrolysis to form a compound of Formula (I); or (C) an electrophlic substrate, in a polar solvent, optionally in the presence of a non-nucleophilic base, to form (17) of the formula

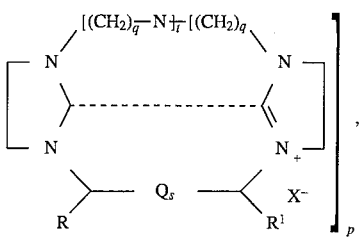 (17)

wherein Q, s, R and $R^1$ are defined as for Formula (I), X is an anion, and the dotted line represents the presence of a bond, t is 0, q is 2 to 3, and p is 1;

followed by prolonged heating in a polar solvent or by treatent with a peroxide solution to form (18) of the formula

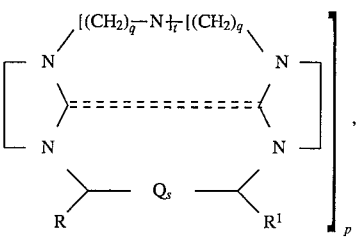 (18)

wherein Q, s, R and $R^1$ are defined as for Formula (I) and the dotted lines represent the presence of a double bond, t is 0, q is 2 to 3, and p is 1;

followed by basic hydrolysis to form the urea (19) of the formula

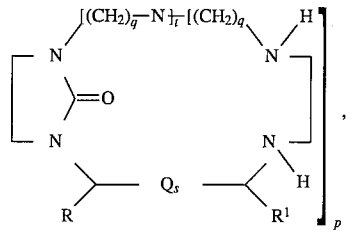 (19)

wherein Q, s, R and $R^1$ are defined as for Formula (I) and t is 0, q is 2 to 3, and p is 1;

then basic hydrolysis under pressure to form a compound of Formula (I); and separating the desired polyazamacrocycle.

2. The process of claim 1 wherein the unsubstituted imidazoline of formula (9) has p is 1, q is 2, and t is 0, which is formula (9a).

3. The process of claim 1, Step (A), wherein the unsubstituted imidazoline of formula (9) has p is 1, q is 2, and t is 0, and the alcohol formed is a compound of the formula

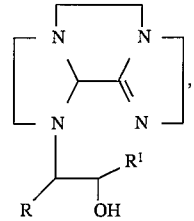 (16a)

where R and $R^1$ are hydrogen, and the intramolecular amination formed a compound of the formula

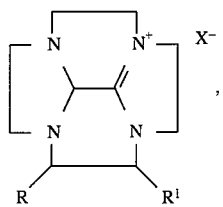
(17a)

where R and R¹ are hydrogen
X is OH or halogen.

4. The process of claim 1, Step (B), wherein the unsubstituted imidazoline of formula (9) has p is 1, q is 2, and t is 0, and the salt formed is a compound of the formula

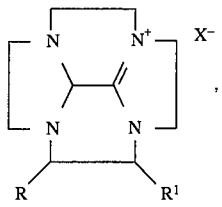
(17a)

where R and R¹ are defined as above, and X is OH or halogen, and the resulting product of Formula (I) is a compound of formula (6).

5. The process of claim 1, Step A, wherein the aprotic solvent is dimethylformamide or diglyme.

6. The process of claim 1, Step A, wherein the reaction is done at from about 100° to about 200° C.

7. The process of claim 1, Step A or B, wherein the basic hydrolysis is done with aqueous sodium hydroxide at a temperature from about 25° to about 200° C.

8. The process of claim 1 wherein the imidazole is 1,1'-(1,2-ethanediyl)-bis[4,5-dihydro-1H]-imidazoline.

9. The process of claim 1 wherein the imidazole is 1,2-ethanyl-2-[4,5-dihydro-1H]-imidazoline.

10. The process of claim 1 wherein the electrophilic substrate is 1,2-dibromoethane, 1,2-dichlorethane or tosylates, mesylates, or triflates of ethylene glycol.

11. The process of claim 1 wherein the electrophilic substrate is ethylene oxide, the imidazole is 1,1'-(1,2-ethanediyl)-bis[4,5-dihydro-1H]-imidazoline and product prepared is

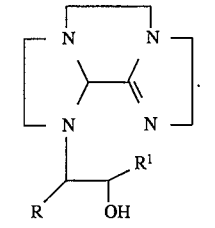
(16a)

12. The process of claim 1 wherein the electrophilic substrate is 1,2-dibromoethane, the imidazole is 1,1'-(1,2-ethanediyl)-bis[4,5-dihydro-1H]-imidazoline, and the product prepared is 1,4,7,10-tetrazacyclododecane.

13. The process of claim 12 wherein the non-aqueous solvent is toluene, diglyme, tetrahydrofuran, dimethylsulfoxide, dimethylformamide, n-propanol, acetonitrile, isopropanol, t-butanol or acetone.

14. The process of claim 1 wherein the electrophilic substrate is 1,2-dibromoethane or 1,2-dichlorethane, or tosylates, mesylates or triflates of ethylene glycol, the imidazole is derived from diethylenetriamine, and the product prepared is triazamacrocyclo-1,4,7-triazacyclononane.

15. The process of claim 1 wherein the electrophilic substrate is 2,3-dibromosuccinic acid, the imidazoline is

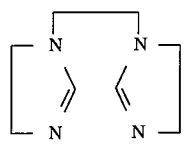
(9)

and the product prepared is 2,3-dicarboxyltetraazacyclododecane.

16. A process for preparing a compound of the formula

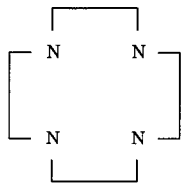
(6)

which comprises reacting an imidazoline of formula (9a)

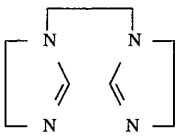
(9a)

with an electrophlic substrate, in a polar solvent, at an elevated temperature, optionally in the presence of a non-nucleophilic base, to form a compound of the formula

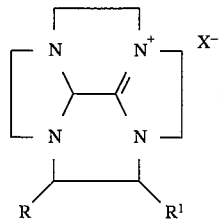
(17a)

where R and R¹ are defined as in claim 1, X is OH or halogen, followed by prolonged heating in a polar solvent or by treatment with a peroxide solution to form a compound of the formula

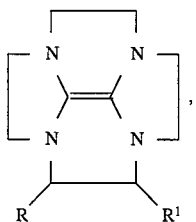
(18a)

where R and R¹ are defined as in claim 1, followed by basic hydrolysis to form a urea of the formula

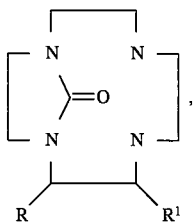
(19a)

where R and R¹ are defined as in claim 1, and then basic hydrolysis under pressure to form a compound of formula (6); and
separating the desired polyazamacrocycle.

17. The process of claim 16, wherein the polar solvent is dimethylformamide, ethylene glycol dimethyl ether, dimethylsulfoxide, acetonitrile, isopropanol, n-propanol, t-butanol or diglyme.

18. The process of claim 16, wherein the temperature is from about 60° to about 160° C.

19. The process of claim 16, wherein the basic hydrolysis or basic hydrolysis under pressure is done with aqueous sodium hydroxide at a temperature from about 100° to about 200° C.

20. The process of claim 1, Step (B), wherein the electrophilic substrate is 1,2-dibromoethane, which is reacted with an imadizoline (10) of the formula

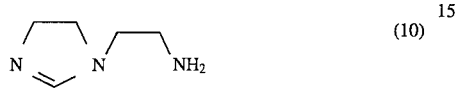 (10)

followed by basic hydrolysis, to yield a 1,4,7-triazacyclononane (22) of the formula

 (22)

which is a compound of Formula (I).

21. The process of claim 1, wherein the electrophilic substrate is 1,3-dichloroacetone, which is reacted with an imadizoline (9) where p equal to 1, q equal to 2, and t equal 0 to yield a cyclic ketone (25) of the formula

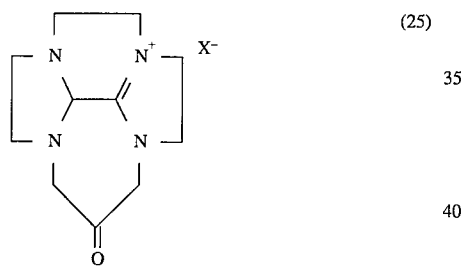 (25)

where X is OH or halogen followed by basic hydrolysis to yield (26) of the formula

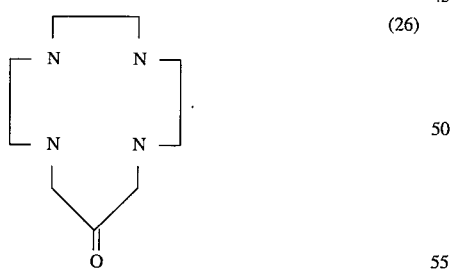 (26)

which is a compound of Formula (I).

22. A compound having the formula:

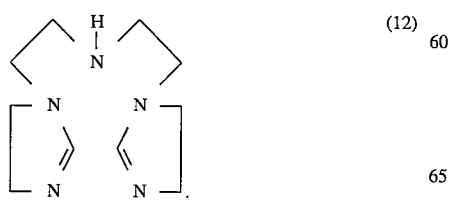 (12)

23. A compound having the formula:

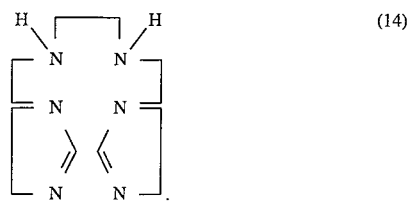 (14)

24. A compound having the formula:

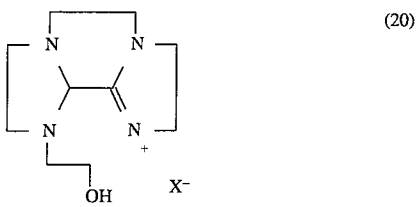 (20)

where X is OH or halogen.

25. A compound having the formula:

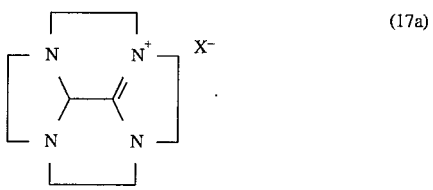 (17a)

where X is OH or halogen.

26. A compound having the formula:

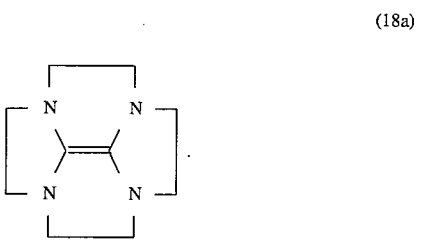 (18a)

27. A compound having the formula:

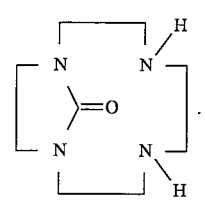 (19a)

28. A compound having the formula:

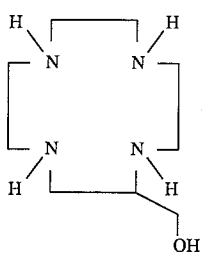 (21a)

29. A compound having the formula:
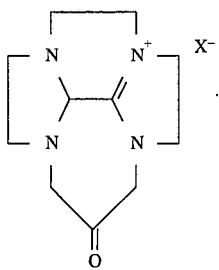
(25)
where X is OH or halogen.
30. A compound having the formula:
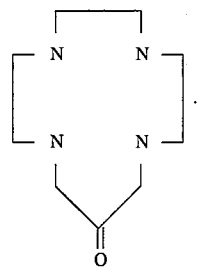
(26)
* * * * *